United States Patent [19]

Matzner et al.

[11] Patent Number: 4,959,424

[45] Date of Patent: Sep. 25, 1990

[54] AMINO-TERMINATED POLY(ARYL ETHER KETONES)

[75] Inventors: Markus Matzner, Edison, N.J.; Donald M. Papuga, Ridgefield, Conn.

[73] Assignee: Amoco Corporation, Chicago, Ill.

[21] Appl. No.: 889,203

[22] Filed: Jul. 25, 1986

[51] Int. Cl.⁵ .................... C08G 65/00; C08G 10/00; C08G 16/00

[52] U.S. Cl. .................... 525/471; 528/126; 528/125

[58] Field of Search ........................ 525/471

[56] References Cited

U.S. PATENT DOCUMENTS

| | | | |
|---|---|---|---|
| 3,503,931 | 3/1970 | Radlmann et al. | 525/467 |
| 3,563,951 | 2/1971 | Radlmann et al. | 528/26 |
| 4,540,748 | 9/1985 | Matzner | 528/126 |
| 4,608,404 | 8/1986 | Gardner et al. | 528/90 |
| 4,656,207 | 4/1987 | Jabloner et al. | 528/93 |
| 4,695,612 | 9/1987 | Takekoshi et al. | 525/471 |
| 4,746,718 | 5/1988 | Gardner et al. | 528/98 |
| 4,789,722 | 12/1988 | Jabloner et al. | 528/172 |

FOREIGN PATENT DOCUMENTS 1388650  1/1965  France ........................ 528/128

OTHER PUBLICATIONS

Houben-Weyl, Nitrogen Compounds-II (11/1), pp. 32-33, Georg Thieme Verlag, Stuttgart, 1957.

*Primary Examiner*—Morton Foelak
*Assistant Examiner*—Frederick Krass
*Attorney, Agent, or Firm*—Frederick S. Jerome; William H. Magidson; Ralph C. Medhurst

[57] ABSTRACT

Described herein are novel amino-terminated poly(aryl ether ketone) oligomers and methods for their production. These amino-terminated poly(aryl ether ketone) oligomers are used as building blocks for a variety of polymers and copolymers.

10 Claims, No Drawings

AMINO-TERMINATED POLY(ARYL ETHER KETONES)

FIELD OF THE INVENTION

This invention is directed to novel amino-terminated poly(aryl ether ketone) oligomers. Processes for the preparation of the subject oligomers are also described. The novel diamino-poly(aryl ether ketones) are useful building blocks for a variety of polymers and copolymers.

BACKGROUND OF THE INVENTION

Poly(aryl ether ketone)s are a known class of engineering polymers. Several poly(aryl ether ketone)s are highly crystalline with melting points above 300° C. Two of these crystalline poly(aryl ketone)s are commercially available and are of the following structure:

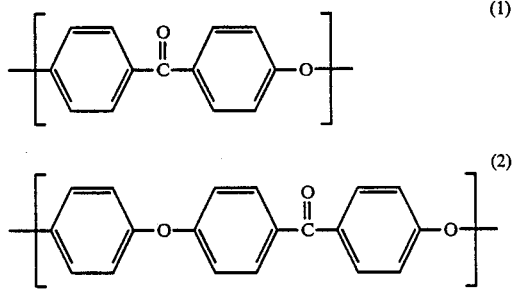

Over the years, there has been developed a substantial body of patent and other literature directed to the formation and properties of poly(aryl ethers) (hereinafter called "PAE"). Some of the earliest work such as by Bonner, U.S. No. 3,065,205, involves the electrophilic aromatic substitution (viz. Friedel-Crafts catalyzed) reaction of aromatic diacylhalides with unsubstituted aromatic compounds such as diphenyl ether. The evolution of this class to a much broader range of PAEs was achieved by Johnson et al., Journal of Polymer Science, A-1, vol. 5, 1967, pp. 2415-2427, Johnson et al., U.S. Pat. Nos. 4,108,837, and 4,175,175. Johnson et al. show that a very broad range of PAEs can be formed by the nucleophilic aromatic substitution (condensation) reaction of an activated aromatic dihalide and an aromatic diol. By this method, Johnson et al. created a host of new PAEs including a broad class of poly(aryl ether ketones), hereinafter called "PAEK's".

In recent years, there has developed a growing interest in PAEK's as evidence by Dahl, U.S. Pat. No. 3,953,400; Dahl et al., U.S. Pat. No. 3,956,240; Dahl, U.S. Pat. No. 4,247,682; Rose et al., U.S. Pat. no. 4,320,224; Maresca, U.S. Pat. No. 4,339,568; Attwood et al., Polymer, 1981, vol 22, August, pp. 1096-1103; Blundell et al., Polymer, 1983, vol. 24, August, pp. 953-958, Attwood et al., Polymer Preprints, 20, No. 1, April 1979, pp. 191-194; and Rueda et al., Polymer Communications, 1983, vol. 24, September, pp. 258-260. In early to mid-1970, Raychem Corp. commercially introduced a PAEK called STILAN ™, a polymer whose acronym is PEK, each ether and keto group being separated by 1,4-phenylene units. In 1978, Imperial Chemical Industries PLC (ICI) commercialized a PAEK under the trademark Victrex PEEK. As PAEK is the acronym of poly(aryl ether ketone), PEEK is the acronym of poly(ether ether ketone) in which the phenylene units in the structure are assumed.

Thus, PAEK's are well known; they can be synthesized from a variety of starting materials; and they can be made with different melting temperatures and molecular weights. The PAEK's are crystalline, and as shown by the Dahl and Dahl et al. patents, supra, at sufficiently high molecular weights they can be touch, i.e., they exhibit high values (>50 ft-lbs/in$^2$) in the tensile impact test (ASTM D-1822). They have potential for a wide variety of uses, but because of the significant cost to manufacture them, they are expensive polymers. Their favorable properties class them in the upper bracket of engineering polymers.

PAEK's may be produced by the Friedel-Crafts catalyzed reaction of aromatic diacylhalides with unsubstituted aromatic compounds such as diphenyl ether as described in, for example, U.S. Pat. No. 3,065,205. These processes are generally inexpensive processes; however, the polymers produced by these processes have been stated by Dahl et al., supra, to be brittle and thermally unstable. The Dahl patents, supra, allegedly depict more expensive processes for making superior PAEK's by Friedel-Crafts catalysis. In contrast, PAEK's such as PEEK made by nucleophilic aromatic substitution reactions are produced from expensive starting fluoro monomers, and thus would be classed as expensive polymers.

These poly(aryl ether ketone)s exhibit an excellent combination of properties; i.e., thermal and hydrolytic stability, high strength and toughness, wear and abrasion resistance and solvent resistance. Thus, articles molded from poly(aryl ether ketones) have utility where high performance is required. However, in some applications where articles having a complex shape are sought fabrication difficulties arise due to the high melt viscosity of the poly(aryl ether ketones).

It is, therefore, often of interest to modify the poly(aryl ether ketones) in a manner such that their excellent properties be retained, but their high melt viscosity reduced to more practical levels. Also, in some applications such as when the poly(aryl ether ketone) is to be used as a thermoplastic composite matrix resin, its glass transition temperature (Tg) may not be as high as desired for the particular application. This is due to the fact that polymers, even crystalline polymers, exhibit excessive loss of modulus, strength and creep resistance above their Tg's. This loss in properties may not be acceptable in cases where the materials are to be used as thermoplastic composite matrix resins. Once again, proper modification of the poly(aryl ether ketone) backbone may become imperative.

THE INVENTION

The present invention is directed to novel diamino-terminated poly(aryl ether ketone) oligomers. Processes for the preparation of the subject materials are also described. The amino functions that are present at both ends of the oligomer chain allow for the incorporation of the latter into a variety of polymers and copolymers wherein the excellent characteristics of the poly(aryl ether ketone) are maintained, and wherein its undesirable features are obviated. An example of such successful modification are the novel polyetherimide polymers, as described in U.S. Pat. No. 4,540,748.

The crystalline poly(aryl ether ketone) oligomers which are suitable for use herein can be generically characterized as containing repeating units of one or more of the following formulae:

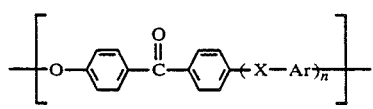

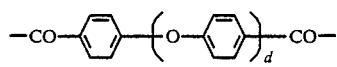

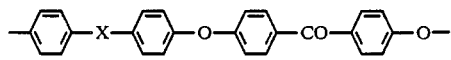

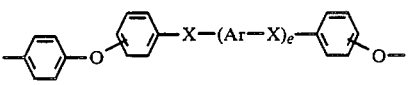

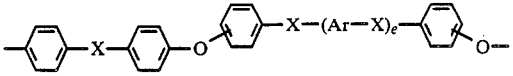

wherein Ar is independently a divalent aromatic radical selected from phenylene, biphenylene or naphthylene, X is independently O,

or a direct bond and is an integer of from 0 to 3, b, c, d and e are 0 to 1 and a is an integer of 1 to 4 and preferably d is 0 when b is 1.

Preferred poly(aryl ketone)s include those having a repeating unit of the formula:

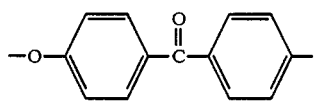

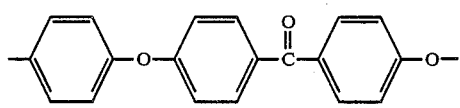

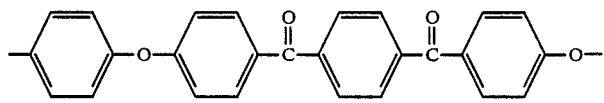

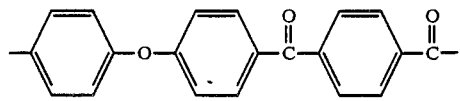

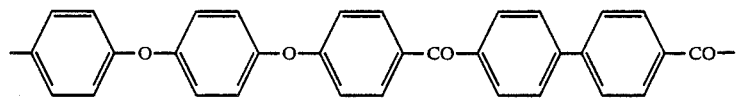

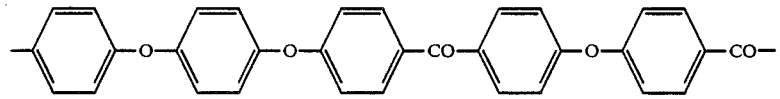

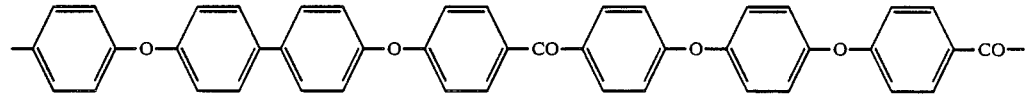

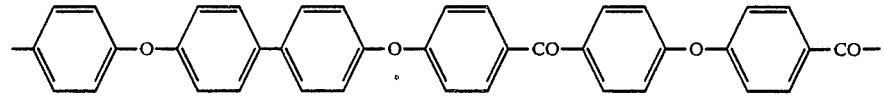

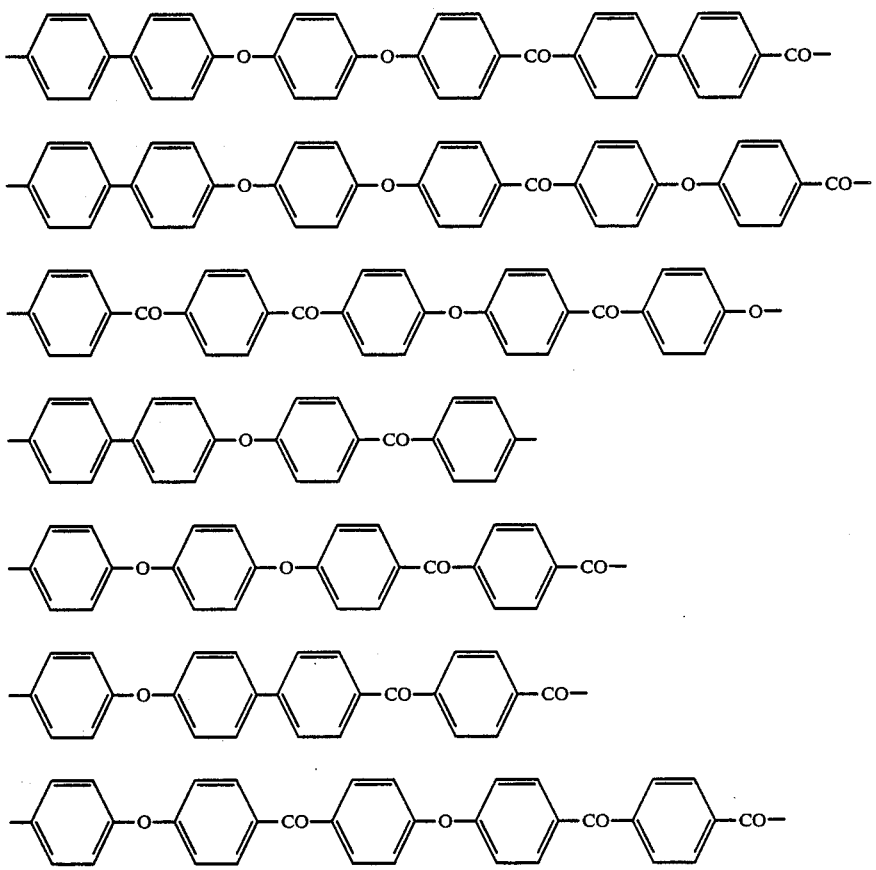

The diamino-poly(aryl ketone) oligomers are prepared from the corresponding dihydroxy- or dihalo-terminated products. The latter are made using methods known in the art. One such method comprises heating at least one bisphenol with at least one dihalobenzenoid compound in the presence of a base. The use of an excess of one of the reagents, i.e., of the bisphenol or of the dihalobenzenoid compound, leads to functionally terminated oligomers having either dihydroxy- or dihalo-termination, respectively. The molecular weight of the oligomers is a function of the excess utilized. The higher the excess of one of the reagents, the lower is the molecular weight of the resulting oligomer.

In another embodiment, the dihydroxy-terminated oligomers may be obtained by hydrolysis of the corresponding dihalo-terminated materials. Conversely, the dihydroxy-end-capped products may be reacted in the presence of base with a molar excess of the dihalobenzenoid compound to yield the dihalo-terminated oligomer.

In still another embodiment, a halophenol may be reacted with itself, and, after reaching the desired molecular weight, reacted with a slight amount of either a bisphenol or a dihalobenzenoid compound to give the respective dihydroxy end-capped or dihalo end-capped oligomers.

Preferred bisphenols in such a process include:
hydroquinone,
4,4'-dihydroxybenzophenone,
4,4'-dihydroxybiphenyl, and
4,4'-dihydroxydiphenyl ether.

Preferred dihalo and halophenol compounds include:
4-(4'-chlorobenzoyl)phenol,
4-(4'-fluorobenzoyl)phenol,
4,4'-difluorobenzophenone,
4,4'-dichlorobenzophenone,
4-chloro-4'-fluorobenzophenone,

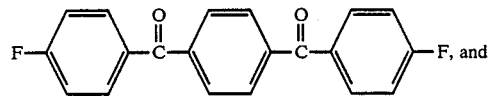

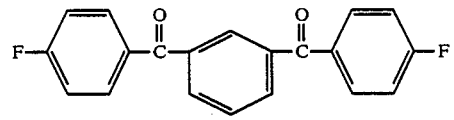

The poly(aryl ketone) oligomers may be produced by the process as described in, for example, U.S. Pat. No. 4,176,222. This process comprises heating in the temperature range of 100° to 400° C., (i) an excess of at least one bisphenol and at least one dihalobenzenoid compound, or (ii) an excess of at least one dihalobenzenoid compound and at least one bisphenol, and/or (iii) at least one halophenol followed by reaction with a small amount of a diphenol or of a dihalobenzenoid compound in order to ensure hydroxyl or halo termination in which in the dihalobenzenoid compound or halophenol, the halogen atoms are activated by —CO— groups ortho or para thereto, with a mixture of sodium carbonate or bicarbonate and a second alkali metal carbonate or bicarbonate, the alkali metal of said second alkali metal carbonate or bicarbonate having a higher atomic number than that of sodium, the amount of said second alkali metal carbonate or bicarbonate being such that there are 0.001 to 0.2 gram atoms of said alkali metal of higher atomic number per gram atom of sodium, the total amount of alkali metal carbonate or bicarbonate being such that there is at least one alkali metal atom for each phenol group present, and thereafter separating the oligomer from the alkali metal halide.

The higher alkali metal carbonates or bicarbonates are thus selected from the group consisting of potassium, rubidium and cesium carbonates and bicarbonates. Preferred combinations are sodium carbonate or bicarbonate with potassium carbonate or cesium carbonate.

The alkali metal carbonates or bicarbonates should be anhydrous although, if hydrated salts are employed, where the polymerization temperature is relatively low, e.g., 100° to 250° C., the water should be removed, e.g., by heating under reduced pressure, prior to reaching the polymerization temperatures.

Where high polymerization temperatures (>250° C.) are used, it is not necessary to dehydrate the carbonate or bicarbonate first as any water is driven off rapidly before it can adversely affect the course of the polymerization reaction. Optionally, an entraining organic medium such as toluene, xylene, chlorobenzene and the like, can be used to remove water from the reaction mixture.

The total amount of alkali metal carbonate or bicarbonate employed should be such that there is at least 1 atom of alkali metal for each phenol group. Hence, there should be at least 1 mole of carbonate, or 2 moles of bicarbonate, per mole of the aromatic diol.

An excess of carbonate or bicarbonate may be employed. Hence there may be 1 to 1.2 atoms of alkali metal per phenol group. While the use of an excess of carbonate or bicarbonate may give rise to faster reactions, there is the attendant risk of cleavage of the resulting polymer, particularly when using high temperatures and/or the more active carbonates.

As stated above the amount of the second (higher) alkali metal carbonates or bicarbonate employed is such that there are 0.001 to about 0.2 gram atoms of the alkali metal of higher atomic number per gram atom of sodium.

Thus when using a mixture of carbonates, e.g., sodium carbonate and cesium carbonate, there should be 0.1 to about 20 moles of cesium carbonate per 100 moles of sodium carbonate. Likewise when using a mixture of a bicarbonate and a carbonate, e.g., sodium bicarbonate and potassium carbonate, there should be 0.05 to 10 moles of potassium carbonate per 100 moles of sodium bicarbonate.

A mixed carbonate, for example sodium and potassium carbonate, may be employed as the second alkali metal carbonate. In this case, where one of the alkali metal atoms of the mixed carbonate is sodium, the amount of sodium in the mixed carbonate should be added to that in the sodium carbonate when determining the amount of the mixed carbonate to be employed.

Preferably, from 0.005 to 0.1 gram atoms of the alkali metal of the second alkali metal carbonate or bicarbonate per gram atom of sodium is used.

The reaction is carried out in bulk or in the presence of an inert solvent.

Preferably the solvent employed is an aliphatic or aromatic sulfoxide or sulfone of the formula $$R-S(O)_x-R'$$

where x is 1 or 2 and R and R' are alkyl or aryl groups and may be the same or different. R and R' may together form a divalent radical. Preferred solvents include dimethyl sulfoxide, dimethyl sulfone, sulfolane (1,1-dioxothiolan), or aromatic sulfones of the formula:

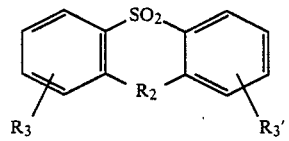

where $R_2$ is a direct link, an oxygen atom or two hydrogen atoms (one attached to each benzene ring) and $R_3$ and $R'_3$, which may be the same or different, are hydrogen atoms and alkyl or phenyl groups. Examples of such aromatic sulfones include diphenylsulfone, dibenzothiophen dioxide, phenoxathiin dioxide and 4-phenylsulfonyl biphenyl. Diphenylsulfone is the preferred solvent.

The polymerization temperature is in the range of from about 100° to about 400° C. and will depend on the nature of the reactants and the solvent, if any, employed. The preferred temperature is above 270° C. The reactions are generally performed under atmospheric pressure. However, higher or lower pressures may be used.

For the production of some oligomers, it may be desirable to commence polymerization at one temperature, e.g., between 200° and 250° C. and to increase the temperature as polymerization ensues. This is particularly necessary when making oligomers having only a low solubility in the solvent. Thus, it is desirable to increase the temperature progressively to maintain the oligomer in solution as its molecular weight increases.

To minimize cleavage reactions it is preferred that the maximum polymerization temperature be below 350° C.

This invention is also directed to an improved process for making the oligomers in comparatively shorter reaction times overall than by using potassium fluoride alone or by using a combination of sodium carbonate or bicarbonate and a second higher alkali metal carbonate or bicarbonate.

Specifically, this process is directed to preparing the poly(aryl ether ketone) precursors by the reaction of a mixture of an excess of the diphenol and of the aromatic activated dihalo compound or, conversely, of an excess of the aromatic activated dihalo compound and of the diphenol, and/or of the activated halophenol followed by reaction with a small amount of a diphenol or of a dihalobenzenoid compound in order to ensure dihydroxy or dihalo termination, in which in the dihalobenzenoid compound or halophenol, the halogen atoms are activated by —CO— groups' ortho or para thereto in the presence of a combination of sodium carbonate and/or bicarbonate and an alkali metal halide selected from potassium, rubidium, or cesium fluoride or chloride, or combinations thereof.

The reaction is carried out by heating a mixture of the reactants as described herein, at a temperature of from about 100° to about 400° C. The reaction is conducted in the presence of added sodium carbonate and/or bicarbonate and potassium, rubidium or cesium fluorides or chlorides. The sodium carbonate or bicarbonate and the chloride and fluoride salts should be anhydrous although, if hydrated salts are employed, where the reaction temperature is relatively low, e.g., 100° to 250° C., the water should be removed, e.g., by heating under reduced pressure, prior to reaching the reaction temperature.

Where high reaction temperatures (>250° C.) are used, it is not necessary to dehydrate the carbonate, bicarbonate, the chloride or fluoride salts first as any water is driven off rapidly before it can adversely affect the course of the reaction. Optionally, an entraining organic medium can be used to remove water from the reaction such as toluene, xylene, chlorobenzene, and the like.

The total amount of sodium carbonate or bicarbonate and potassium, rubidium or cesium fluoride or chloride, or combinations thereof employed should be such that there is at least 1 atom of total alkali metal for each phenol group, regardless of the anion (carbonate, bicarbonate or halide).

Preferably, from about 1 to about 1.2 atoms of the total alkali metal for each phenol group is used. In another preferred embodiment from about 0.001 to about 0.5 atoms of alkali metal (derived from a higher alkali metal halide) is used for each phenol group.

The sodium carbonate or bicarbonate and the potassium, rubidium or cesium fluoride are used such that the ratio of potassium, rubidium or cesium to sodium therein is from about 0.001 to about 0.5, preferably from about 0.01 to about 0.25, and most preferably from about 0.02 to about 0.20.

An excess of total alkali metal may be employed. Hence there may be about 1 to about 1.7 atoms of alkali metal per phenol group. While the use of a large excess of alkali metal may give rise to faster reactions, there is the attendant risk of cleavage of the resulting polymer, particularly when using high temperatures and/or the more active alkali metal salts. Of course it is well known to those skilled in the art that cesium is a more active metal and potassium is a less active metal so that less cesium and more potassium are used. Further, the chloride salts are less active than the fluoride salts so that more chloride and less fluoride is used.

The reactions are carried out in bulk or in the presence of an inert solvent.

Preferably the solvent employed is an aliphatic or aromatic sulfoxide or sulfone of the formula R—S(O)$_x$—R′ where x is 1 or 2 and R and R′ are alkyl or aryl groups and may be the same or different. R and R′ may together form a divalent radical. Preferred solvents include dimethyl sulfoxide, dimethyl sulfone, sulfolane (1,1-dioxothiolan), or aromatic sulfones of the formula:

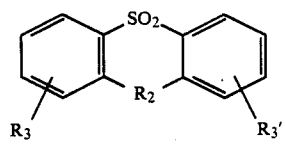

where R$_2$ is a direct link, an oxygen atom or two hydrogen atoms (one attached to each benzene ring) and R$_3$ and R′$_3$, which may be the same or different, are hydrogen atoms and alkyl or phenyl groups. Examples of such aromatic sulfones include diphenylsulfone, dibenzothiophen dioxide, phenoxathiin dioxide and 4-phenylsulfonyl biphenyl. Diphenylsulfone is the preferred solvent.

The reaction temperature is in the range of from about 100° to about 400° C. and will depend on the nature of the reactants and the solvent. The preferred temperature is above 250° C. The reactions are preferably carried out at ambient pressure. However, higher or lower pressures can also be used. The reaction is generally carried out in an inert atmosphere.

For the production of some oligomers it may be desirable to commence reaction at one temperature, e.g., between 200° and 250° C. and to increase the temperature as reaction ensues. This is particularly necessary when making higher molecular weight oligomers having only a low solubility in the solvent. Thus, there it is desirable to increase the temperatures progressively to maintain the oligomer in solution as its molecular weight increases.

To minimize cleavage reactions it is preferred that the maximum polymerization temperature be below 350° C.

Also, poly(aryl ketone) oligomers such as those containing repeating units of the formula:

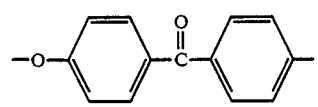

may be produced by Friedel-Crafts reactions utilizing hydrogen fluoride-boron trifluoride catalysts as described, for example, in U.S. Pat. No. 3,953,400.

Additionally, poly(aryl ketone) oligomers of the following formula:

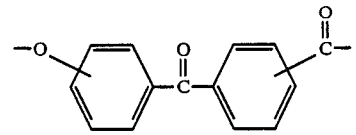

may be prepared by Friedel-Crafts reactions using a boron fluoride-hydrogen fluoride catalyst as described in, for example, U.S. Pat. Nos. 3,441,538; 3,442,857 and 3,516,966.

Additionally, the oligomers may be prepared by Friedel-Crafts processes as described in, for example, U.S. Pat. Nos. 3,065,205; 3,419,462; 3,441,538; 3,442,857; 3,516,966; and 3,666,612. In these patents a PAEK is produced by Friedel-Crafts polymerization techniques using Friedel-Crafts catalysts such as aluminum trichloride, zinc chloride, ferric bromide, antimony pentachloride, titanium tetrachloride, etc. and a solvent.

The preferred Friedel-Crafts catalysts are aluminum chloride, antimony pentachloride and ferric chloride. Other Friedel-Crafts catalysts, such as aluminum bromide, boron trifluoride, zinc chloride, antimony trichloride, ferric bromide, titanium tetrachloride, and stanic chloride, can also be used. In the preferred embodiment, an excess of up to 100 mole percent of the acid catalyst is used.

The polymerization is generally carried out in the presence of a solvent. The preferred organic solvent is 1,2-dichloroethane. Other solvents such as symmetrical tetrachloroethane, o-dichlorobenzene hydrogen fluoride, methylene chloride, trichloromethane, trichloroethylene, or carbon disulfide may be employed. Cosolvents such as nitromethane, nitropropane, dimethyl formamide, sulfolane, etc. may be used. Concentrations as low as 3 to as high as 40 weight percent may be used. Generally lower concentrations are preferred when higher molecular weight oligomers are being prepared. Higher concentrations are preferably used when low molecular weight oligomers are prepared.

The reaction may be carried out over a range of temperatures which are from about −40° C. to about 160° C. In general, it is preferred to carry out the reaction at a temperature in the range of 0° to 30° C. In some cases it is advantageous to carry out the reaction at temperatures above 30° C. or below 0° C. Most preferably, the reactions are carried out at temperatures below 0° C. The reaction may be carried out at atmospheric pressure although higher or lower pressures may be used. Reaction times vary depending on the reactants, etc. Generally, reaction times of up to 6 hours and longer are preferred.

The polyketone oligomers may also be prepared according to the process as described in, for example, U.S. Defensive Publication T 103,703 and U.S. Pat. No. 4,396,755. In such processes, reactants such as (a) an aromatic monocarboxylic acid, (b) a mixture of at least one aromatic dicarboxylic acid, and an aromatic hydrocarbon, and (c) combinations of (a) and (b) are reacted in the presence of a fluoroalkane sulphonic acid, particularly trifluoromethane sulphonic acid.

Additionally, poly(aryl ether ketone) oligomers of the following formulas:

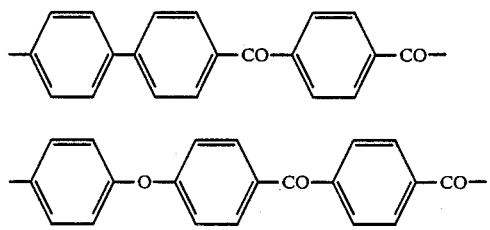

may also be prepared according to the process as described in, for example, U.S. Pat. No. 4,398,020. In such a process, (a) a mixture of
(i) at least one aromatic diacyl halide of the formula:

where —Ar$_1$— is a divalent aromatic radical, Y is halogen and COY is an aromatically bound acyl halide group, which diacyl halide is polymerizable with at least one aromatic compound of (a)(ii), and (ii) at least one aromatic compound of the formula:

wherein —Ar$_2$— is a divalent aromatic radical and H is an aromatically bound hydrogen atom, which compound is polymerizable with at least one diacyl halide of (a)(i), or (b) at least one aromatic monoacyl halide of the formula:

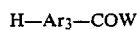

where —Ar$_3$— is a divalent aromatic radical and H is an aromatically bound hydrogen atom, W is halogen, and COW is an aromatically bound acyl halide group, which monoacyl halide is self-polymerizable, or (c) a combination of (a) and (b) is reacted in the presence of a fluoroalkane sulphonic acid.

In order to obtain oligomers having the desired dihydroxyl or dihalo termination, appropriate capping agents must be used in the Friedel-Crafts catalyzed reactions described above. This can be accomplished as shown.

Variant 1

In this variant, a diacid dihalide, is polycondensed with a hydrocarbon reactant. An excess of the dihalide is used; reaction of the acid halide-terminated

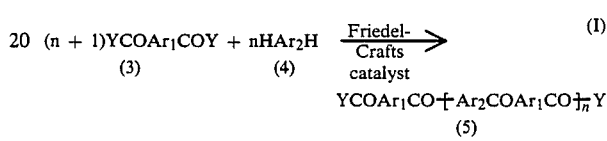

intermediate (5) with a halohydrocarbon (6) yields the dihalo-terminated oligomer (7). Hydrolysis of the latter yields the desired dihydroxy poly(aryl ether ketone) oligomer (8).

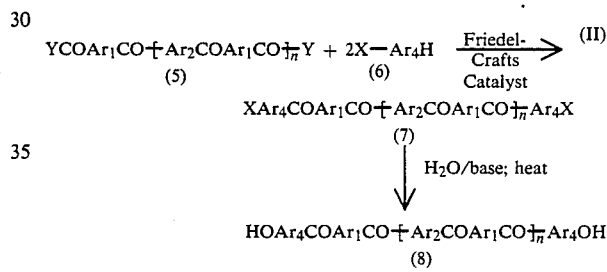

In the above equations Y, Ar$_1$ and Ar$_2$ are as defined above. The group Ar$_4$ is a divalent aromatic radical, preferably paraphenylene; X is halogen, preferably chlorine or fluorine. Other preferred halohydrocarbons (6) are those represented by the formulae (9)–(11).

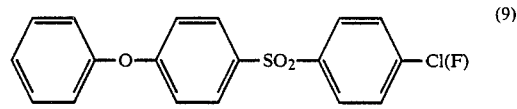

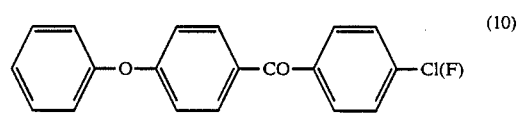

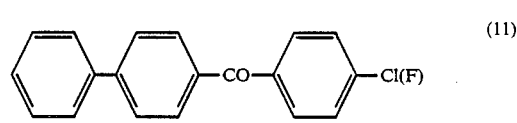

Variant 2

In this variant an excess of hydrocarbon is condensed with the diacid halide. The intermediate (12) is then reacted with a halo-substituted monoacid halide (13) to give the halo-terminated oligomer (14). Hydrolysis of the latter leads to the

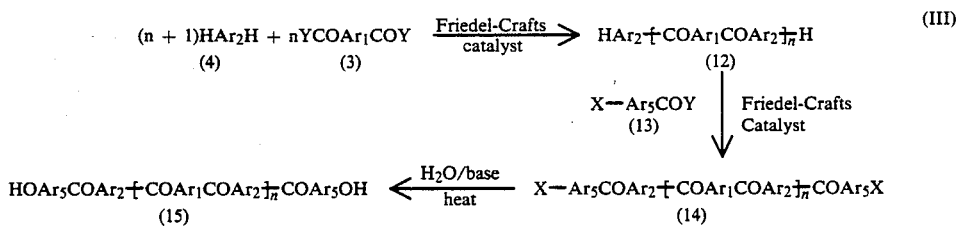

$$(n + 1)HAr_2H + nYCOAr_1COY \xrightarrow{\text{Friedel-Crafts}}_{\text{catalyst}} HAr_2+COAr_1COAr_2]_nH \quad (III)$$
$$(4) \qquad (3) \qquad\qquad (12)$$

$$\qquad\qquad X-Ar_5COY \quad \bigg| \quad \text{Friedel-Crafts}$$
$$\qquad\qquad (13) \qquad\qquad \text{Catalyst}$$

$$HOAr_5COAr_2+COAr_1COAr_2]_nCOAr_5OH \xleftarrow{\text{H}_2\text{O/base}}_{\text{heat}} X-Ar_5COAr_2+COAr_1COAr_2]_nCOAr_5X$$
$$(15) \qquad\qquad\qquad\qquad\qquad (14)$$

terminated poly(aryl ether ketone) oligomer (15).

In the above equations X, Y, Ar₁ and Ar₂ are as defined above; Ar₅ is a divalent aromatic radical, preferably p-phenylene. Other preferred X—Ar₅COY are for example (16) and (17).

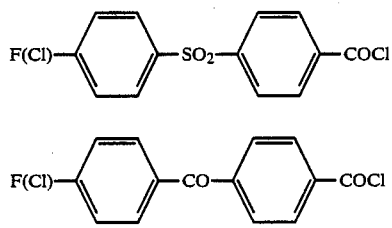

(16)

(17)

Variant 3

In this variant an aromatic monoacyl halide is polymerized in the presence of a Friedel-Crafts catalyst to the oligomer stage (19). The oligomer (19) is then end-capped

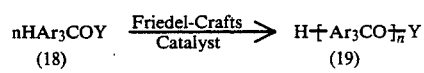

(IV)

by both XAr₄H and XAr₅COY as shown:

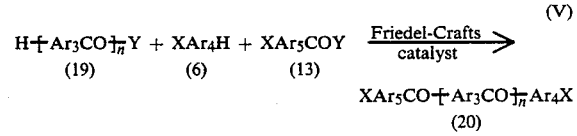

(V)

$$XAr_5CO+Ar_3CO]_nAr_4X$$
$$(20)$$

Hydrolysis of (20) yields the dihydroxy-terminated poly(aryl ether ketone) oligomer (21).

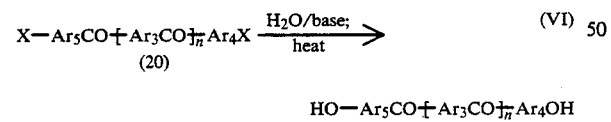

(VI)

$$HO-Ar_5CO+Ar_3CO]_nAr_4OH$$
$$(21)$$

In the above equations Ar₃, Ar₄, Ar₅, X, and Y are as defined above.

For all three variants the value of n should be such that the number average molecular weight of the oligomer be at least 500, preferably at least 1,000, and most preferably at least 1,200.

Specifically, the precursor oligomers may be prepared by reacting any of the well-known aromatic co-reactants such as diphenyl sulfide, dibenzofuran, thianthrene, phenoxathiin, dibenzodioxine, phenodioxin, diphenylene, 4,4'-diphenoxybiphenyl, xanthone, 2,2'-diphenoxybiphenyl, 1,4-diphenoxybenzene, 1,3-diphenoxybenzene, 1-phenoxynapthalene, 1,2-diphenoxynapthalene, diphenoxybenzophenone, diphenoxy dibenzoyl benzene, diphenyl ether, 1,5-diphenoxynapthalene, and the like. Among these, diphenyl ether, diphenyl, diphenyl methane, 1,4-diphenoxy benzene, and 4,4'-diphenoxy diphenyl ether are preferred.

Similarly, the following compounds are diacyl halides which may be used as reactants: terephthaloyl chloride, isophthaloyl chloride, thio-bis(4,4'-benzoyl chloride), benzophenone-4,4'-di(carbonyl chloride), oxy-bis(3,3'-benzoyl chloride), diphenyl-3,3-'-di(carbonyl chloride), carbonyl-bis(3,3'-benzoyl chloride), sulfonyl-bis(4,4'-benzoyl chloride), sulfonyl-bis(3,3'-benzoyl chloride), sulfonyl-bis(3,4'-benzoyl chloride), thio-bis(3,4'-benzoyl chloride), diphenyl-3,4'-di(carbonyl chloride), oxy-bis[4,4'-(2-chlorobenzoyl chloride)], naphthalene-1,6-di(carbonyl chloride), naphthalene-2,5-di(carbonyl chloride), naphthalene-2,6-di(carbonyl chloride), oxy-bis[7,7'-naphthalene-2,2'-di(carbonyl chloride)], thio-bis[8,8'-naphthalene-1,1-di(carbonyl chloride)], [7,7'-binaphthyl-2,2-di(carbonyl chloride)], diphenyl-4,4'-di(carbonyl chloride), carbonyl-bis[7,7'-naphthalene-2,2'-di(carbonyl chloride)], sulfonyl-bis[6,6'-naphthalene-2,2'-di(carbonyl chloride)], dibenzofuran-2,7-di(carbonyl chloride) and the like.

Illustrative of suitable acyldihalides include carbonyl chloride (phosgene), carbonyl bromide, carbonyl fluoride and oxalyol chloride.

Preferably, diphenyl ether and/or diphenoxybenzene are reacted with terephthaloyl chloride and/or phosgene.

As mentioned before, the dihydroxy or dihalo end-capped poly(aryl ether ketone) blocks have number average molecular weights of at least 500, preferably of at least 1,000, and most preferably of at least 1,200.

The diamino-terminated oligomers are prepared from the corresponding dihydroxy- or dihalo-end-capped materials via the methods described below.

Method I.

A dihalo-terminated poly(aryl ether ketone) is reacted with an aminophenol in the presence of base. The reaction is exemplified using oligomer (14) (equation VII)).

$$X-Ar_5COAr_2+COAr_1COAr_2]_nCOAr_5X + \quad (VII)$$
$$(14)$$

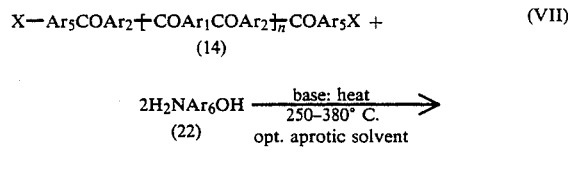

$$H_2NAr_6OAr_5COAr_2+COAr_1COAr_2]_nCOAr_5OAr_6NH_2$$
$$(23)$$

In the equation above Ar₁, Ar₂, and Ar₅ are as defined above; X is as defined above and is preferably fluorine;

$Ar_6$ is a divalent aromatic radical such as p-phenylene, m-phenylene, 4,4'-biphenylene, naphthylene, and the like.

The reaction depicted in equation (VII) can be performed in bulk or in solution. It is preferably conducted in an aprotic solvent. The conditions, i.e., base, solvents, etc., are the same as those described for the nucleophilic preparation of the starting dihalo-terminated oligomers. The systems sodium carbonate/potassium carbonate or sodium carbonate/potassium fluoride are used preferably as the base. Diaryl sulfones, in particular diphenyl sulfone, are the preferred reaction solvents. The preferred temperature range is from about 250° C. to about 350° C., although lower and higher temperatures may also be used. The reactions are preferably run under an inert atmosphere; they are generally conducted under atmospheric pressure; higher and lower pressures can also be applied. In order to ensure proper diamino termination, it is imperative that at least two moles of the aminophenol be employed per mole of the starting dihalo end-capped oligomer. It is preferred, however, to use more than 2 moles of the aminophenol end-capping reagent. Thus, for best results, at least 2.5 moles of the aminophenol and, in some instances, amounts as high as 4 or 5 moles of the aminophenol, should be used per mole of the dihalo oligomer.

The end-capping reaction can be performed in a separate step, i.e., using isolated and purified dihalo-terminated starting material. Alternatively, the end-capping step may be conducted in the same vessel in which the starting material has been prepared by simply adding the aminophenol terminator (and possibly solvent and/or base) to the reaction mixture at the appropriate moment. This variant is particularly useful when the starting dihalo end-capped oligomer is also prepared by the nucleophilic condensation reaction. In still another embodiment, all of the reagents, i.e., the diphenol, the excess of the dihalo benzenoid compound, and the aminophenol are charged into the vessel and polycondensed nucleophilically to the desired diamino-terminated poly(aryl ether ketone).

As mentioned above, the group $Ar_6$ is a divalent $C_1$ to $C_{20}$ aromatic radical optionally substituted with an inert group, i.e., a $C_1$ to $C_7$ alkyl group, a $C_5$ to $C_{12}$ cycloalkyl group, or a halogen. Preferred amino-phenols are shown (structures (24)-(28)).

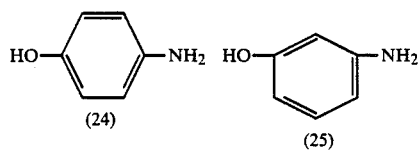

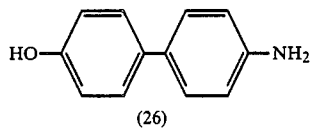

(26)

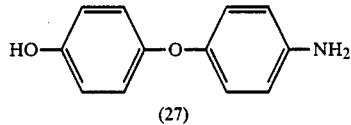

(27)

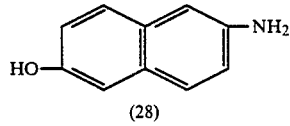

(28)

Method II

This method involves a condensation step of the dihydroxy-terminated oligomer with a halo-nitroaromatic compound, followed by the reduction of the nitro function to the corresponding amino function. The sequence is illustrated in equation (VIII) using oligomer (8).

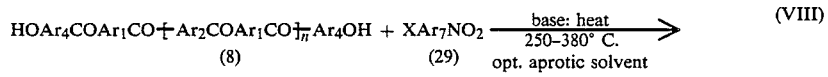 (VIII)

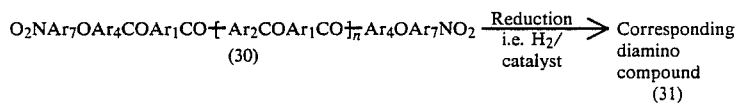

In the equation above $Ar_1$, $Ar_2$, $Ar_4$, and $X$ are as defined above; the group $Ar_7$ is a divalent aromatic radical such as p-phenylene; $X$ and $NO_2$ are in a para- or ortho-configuration. The group $Ar_7$ may carry additional substituents such as additional halo functions and/or additional nitro functions. In this latter case, reduction will lead to tetraamino, or generally polyamino, terminated poly(aryl ether ketones). The group $Ar_7$ may also carry alkyl ($C_1$ to $C_7$) and cycloalkyl ($C_5$ to $C_{12}$) substituents. This is less desirable, however, due to the deactivating effect of these groups on the nucleophilic termination reaction.

The reaction depicted in the first step of equation (VIII) can be performed in bulk or in solution. It is preferably conducted in solution, using an aprotic solvent. The conditions, i.e., base, solvents, etc., are the same as those described for the nucleophilic preparation of the starting dihydroxy-terminated oligomers. The systems sodium carbonate/potassium carbonate or sodium carbonate/potassium fluoride are the preferred bases. Diaryl sulfones, in particular diphenyl sulfone, are the preferred reaction solvents. The preferred temperature range is from about 250° C. to about 350° C., although lower and higher temperatures may also be used. The reactions are preferably run under an inert atmosphere; they are generally conducted under atmospheric pressure; higher and lower pressures can also be applied. In order to ensure proper dinitro or polynitro termination, it is imperative that at least two moles of the halo-nitrobenzenoid compound be employed per mole of the starting dihydroxy end-capped oligomer. It is preferred, however, to use more than 2 moles of the halo-nitrobenzenoid end-capping reagent. Thus, for best results, at least 2.5 moles of the halo-nitrobenzenoid compound and, in some instances, amounts as high as 4 or 5 moles of the halo-nitrobenzenoid compound, should be used per mole of the dihydroxy oligomer.

The end-capping reaction can be performed in a separate step, i.e., using isolated and purified dihydroxy-terminated starting material; or it may be conducted in one step with the preparation of the oligomer. This approach is useful when the oligomer is also prepared by the nucleophilic polycondensation route. The halo-nitro compound may be added to the reaction mixture with all of the ingredients at the start of the oligomer formation. Alternatively, the oligomer may be formed first and, at the appropriate moment, the halo-nitro compound added to affect nitro end-capping. The preferred halo-nitrobenzenoid compound is (32)

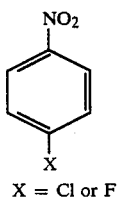

X = Cl or F

The second step of equation (VIII) consists in reducing the nitro compound to the corresponding diamino or polyamino poly (aryl ether ketone). The preferred method of reduction is catalytic, although reductions by other means, e.g., by zinc powder in acid solution, stannous chloride in acid solution, hydrazine, sodium borohydride-sulfur in tetrahydrofuran as described in the *Canadian Journal of Chemistry*, Vol. 49, p. 2990 (1971), etc., may also be useful. The catalytic reductions use preferably palladium (e.g., Pd-C or Pd-BaSO4), platinum, or nickel (e.g., Raney nickel) based catalysts as described in Houben-Weyl, *Methoden der Organischen Chemie*, Volume 11, part I, p. 360 and following, 4th Edition, Georg Thieme Verlag, Stuttgart, 1957. The reactions are performed in solution or in suspension. The preferred hydrogenation solvents are pyridine, dimethylformamide, N-methylpyrolidone, dimethyl acetamide, and diphenyl sulfone, though care must be taken with the latter to avoid sulfur-aromatic ring cleavage. The temperature range for the hydrogenation varies depending on the particular case, from as low as room temperature, to as high as 90° to 100° C., or even higher. In order to avoid formation of secondary products, hydrogen pressures higher than atmospheric are preferred (1.5 to 50 atmospheres, or higher, if necessary).

As mentioned before, the reactions should be performed either in solution or in suspension.

Method III

A third approach whereby the diamino-terminated poly(aryl ether ketones) can be prepared comprises reacting the dihalo-terminated oligomers, e.g. (7), (14), or (20) with ammonia. The reaction is illustrated in equation (IX) using the oligomer (20).

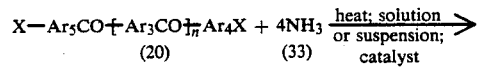

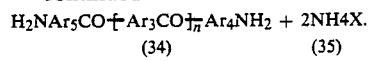

The reaction shown in equation (IX) can be performed either in suspension or in solution. Thus, a finely divided dihalo-terminated poly(aryl ketone) oligomer can be reacted in a suspension of aqueous ammonia at elevated temperatures and pressures. In another embodiment, the dihalo-oligomer is reacted with ammonia in solution; preferred solvents are the dipolar aprotic solvents such as an aromatic or aliphatic sulfoxide or sulfone of the formula:

where x is 1 or 2 and R and $R^1$ are alkyl or aryl groups and may be the same or different. R and $R^1$ may together form a divalent radical. Preferred solvents include dimethyl sulfoxide, dimethyl sulfone, sulfolane (1,1-dioxothiolan), or aromatic sulfones of the formula:

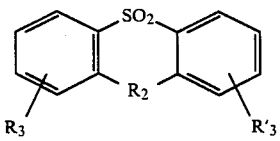

where $R_2$ is a direct link, an oxygen atom or two hydrogen atoms (one attached to each benzene ring) and $R_3$ and $R'_3$, which may be the same or different, are hydrogen atoms and alkyl or phenyl groups. Examples of such aromatic sulfones include diphenyl sulfone, dibenzothiophene dioxide, phenoxathiin dioxide and 4-phenylsulfonyl biphenyl. Diphenyl sulfone is the preferred solvent.

The solution reaction is also performed at high temperatures and pressures. The reaction temperatures both in the suspension and solution variants are in the range of from about 200° to 350° C., the range of from about 250° to 320° C. being preferred.

The reaction shown in equation (IX) can be performed using amines instead of ammonia. Methylamine and phenylamine are of particular interest. A variety of other primary and secondary amines are also useful.

The amination reaction of equation (IX) can be catalyzed with copper$^{(1)}$ salts. Cuprous chloride is preferred. Preferred amounts are in the range of from 0.01 to 5 wt.% of the cuprous salt based on the poly(aryl ketone) oligomers used. After completion of the reaction the catalyst should be removed in order that the thermal stability of the diamino-derivative not be adversely affected. Removal is preferably performed using appropriate chelating agents such as, for example, citric acid.

A certain proportion of keto groups of the starting dihalo-terminated oligomer will react with ammonia to form the corresponding ketimine derivatives. Thus, more than 4 moles of ammonia per mole of oligomer should be used in the amination. Amounts as high as 15 to 20 moles (or even higher) of ammonia per mole of the dihalo-terminated oligomer may have to be used depending on the particular oligomer employed. The ketimine groups are easily converted back to the keto groups via hydrolysis.

The preferred routes to the novel diamines of the instant invention are methods I and III. Method I is the most preferred.

The novel diamino poly(aryl ether ketones) are useful building blocks for a variety of polymers and copolymers. Their usefulness in polyetherimides was recently described in U.S. Pat. No. 4,540,748.

EXAMPLES

The following examples serve to give specific illustrations of the practice of this invention, but they are not intended in any way to limit the scope of this invention.

Preparation of Oligomers

Example 1

A 2000 ml flask was fitted with a mechanical stirrer, nitrogen sparge tube, thermometer, reflux condenser and gas outlet connected to an aqueous sodium hydroxide trap. The apparatus was purged with nitrogen and while under a positive pressure was charged with 1400 ml of 1,2-dichloroethane, 2.03 g (0.010 moles) of isophthaloyl chloride, 38.57 g (0.190 moles) of terephthaloyl chloride, 35.74 g (0.210 moles) of diphenylether and 3.17 g (0.020) moles of p-fluorobenzoyl chloride. The mixture was cooled to 0° C. as 12.80 g (0.546 moles) of aluminum trichloride was added at a rate such as not to exceed 5° C. After 6 hours at 0° C., the heterogeneous slurry was allowed to warm to room temperature (about 25° C.) and stirred for an additional 17 hours. The excess solvent was decanted and the precipitate was added to dilute aqueous acid (3000 ml $H_2O$/100 ml conc. hydrochloric acid) and heated to reflux for 2 hours while the 1,2-dichloroethane was continuously removed. The polymer was filtered and dried in a vacuum oven at 60° C. for 24 hours to give 60.2 grams of the final polymer having a general structure as shown in formula (36). The polymer had a reduced viscosity of 0.34 dl/g as measured in sulfuric acid at a concentration of 1 g/100 ml at 25° C.

Its structure corresponds to formula (36) with n being of about 20 (mol. wt. of about 6,300).

fluorobenzoyl chloride and 600 mls of 1,2-dichloroethane. The mixture was cooled to 0° C. as 174.21 g (1.31 moles) of aluminum trichloride was added at a rate such as not to exceed 5° C. After 6 hours at 0° C. the viscous homogeneous mixture was allowed to warm to room temperature and stirring was continued for an additional 17 hours. The entire mixture was then poured into dilute aqueous acid (3000 ml of $H_2O$/100 ml conc. hydrochloric acid), refluxed with continuous removal of 1,2-dichloroethane and filtered. The precipitate was refluxed in 5% hydrochloric acid (700 ml), filtered, washed at room temperature with distilled water (2 times using 500 ml) and methanol (2 times using 500 ml) and dried in a vacuum oven at 100° C. for 24 hours. The final oligomeric crystalline poly(aryletherketone) had the structural formula (37) and was characterized by $^{13}C$ NMR, by mass spectroscopy and elemental analysis.

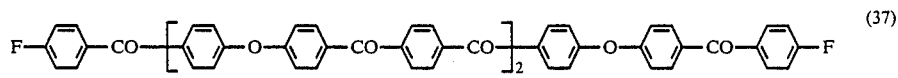
(37)

Example 3

A 250 ml flask was fitted with a mechanical stirrer, nitrogen sparge tube, thermometer, reflux condenser, and gas outlet connected to an aqueous sodium hydroxide trap. The apparatus was purged with nitrogen and while under positive pressure was charged with 96 ml of 1,2-dichloroethane, 11.40 g (0.067 moles) of diphenyl ether, 20.30 g (0.100 moles) of tetrephthaloyl chloride and 6.44 g (0.067 moles) of fluorobenzene. The mixture was cooled to 0° C. as 34.67 g (0.260 moles) of aluminum trichloride was added at such a rate as not to exceed 5° C. After 6 hours at 0° C. the heterogeneous slurry was allowed to warm to room temperature and stirring was continued for an additional 17 hours. The entire mixture was then poured into dilute aqueous acid (300 ml water/100 ml conc. hydrochloric acid) and refluxed for 2 hours with the continuous removal of 1,2-dichloroethane. The resultant precipitate was collected via filtration, refluxed in 5% hydrochloric acid (700 ml), filtered, washed in a blender with distilled water (2 times using 500 ml) followed by methanol (2 times using 500 ml) at room temperature and dried in a vacuum oven at 100° C. for 24 hours. The final oligomeric crystalline poly(aryl ether ketone) having the structural formula (38) was characterized by $^{13}C$ NMR; its structure was also confirmed by mass spectroscopy.

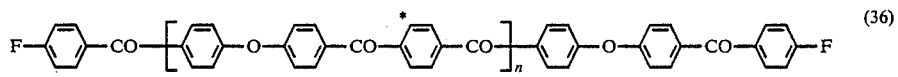
(36)

(*wherein the CO groups are meta and para to each other)

Example 2

A 1000 ml flask was fitted with a mechanical stirrer, reflux condenser, thermometer, nitrogen sparge tube, and gas outlet connected to an aqueous sodium hydroxide trap. The apparatus was purged with nitrogen and while having a positive pressure was charged with 85.11 g (0.500 moles) of diphenylether, 68.01 g (0.335 moles) of terephthaloyl chloride, 53.12 g (0.335 moles) of p-

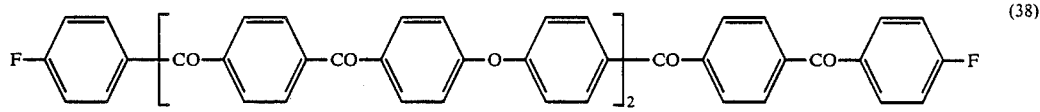
(38)

Example 4

A 100 ml flask was fitted with a mechanical stirrer, reflux condenser, thermometer, nitrogen sparge, and gas outlet connected to an aqueous sodium hydroxide trap. The apparatus was purged with nitrogen and while under a positive pressure was charged with 17.02 g (0.100 moles) of diphenyl ether, 10.15 g (0.050 moles) of terephthaloyl chloride, 15.8 g (0.100 moles) of p-fluorobenzoyl chloride and 48 mls of 1,2-dichloroethane. The mixture was cooled to 0° C. as 34.67 g (0.260 moles) of aluminum trichloride was added at such a rate as not to exceed 5° C. After 6 hours at 0° C. the viscous homogeneous mixture was allowed to warm to room temperature and stirring continued for an additional 17 hours. The entire mixture was then poured into dilute aqueous acid (1300 ml water/50 ml conc. hydrochloric acid), refluxed with continuous removal of 1,2-dichloroethane, and filtered. The precipitate was refluxed in 5% hydrochloric acid (700 ml), filtered, washed at room temperature with water (2 times using 500 ml) and methanol (2 times using 500 ml) and dried in a vacuum oven at 100° C. for 24 hours. The final oligomeric crystalline poly(aryl ether ketone) having the structural formula (39) was characterized by $^{13}$C NMR and its structure confirmed by mass spectroscopy and elemental analysis.

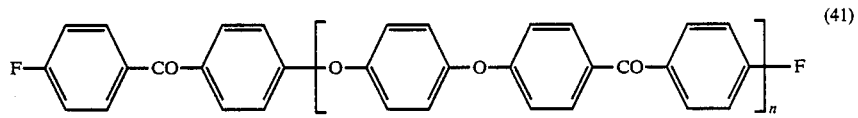

(39)

Example 5

Preparation of the hydroxyl-terminated oligomer (40).

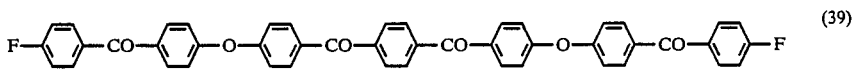

(40)

A 250 ml 3-neck flask with slanted side arms fitted with a Claisen arm, nitrogen inlet tube, thermocouple probe, condenser, and stainless steel stirrer was charged with difluorobenzophenone (0.1104 mole, 24.09 gm), hydroquinone (0.115 mole, 12.66 gm), sodium carbonate (0.1173 moles, 12.43 gm, ground and dried), anhydrous potassium fluoride (0.0293 mole, 1.70 gm) and diphenyl sulfone (100 gm). The apparatus was evacuated and filled with argon by means of a Firestone valve connected to the top of the condenser. A flow of high purity nitrogen was begun and the connection to the Firestone valve was replaced with a bubbler. The contents of the flask were heated carefully by means of a heating mantle and temperature controller to melt the diphenyl sulfone. The reaction mixture was stirred and heated to 200° C. and held 30 minutes at that temperature; it was then held at 250° C. for 1 hour, and finally at 270° C. for 2 hours. The reaction mixture was poured from the reaction flask, cooled, ground to a fine powder, and a sample refluxed successively twice with acetone, once with 2% hydrochloric acid, once with water, and washed thoroughly with acetone. The dried (120°, vacuum oven) sample gave a reduced viscosity (1% in conc. sulfuric acid, 25° C.) of 0.53 dl/gm. Based on reactant stoichiometry this oligomer had the structure (40) as depicted above.

Example 6

A halo-terminated oligomer having structure (41) and wherein n is about 20

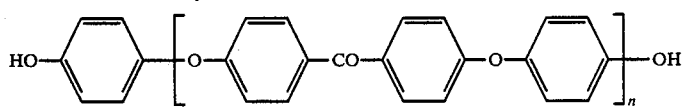

(41)

is prepared in a manner similar to that described in Example 5, except that a suitable molar excess of 4,4'-difluorobenzophenone is used.

Example 7

End-capping of oligomers—general technique

A 250 ml flask is fitted with a mechanical stirrer, nitrogen inlet, thermocouple controller and a Dean Stark trap with a condenser. The flask is charged with 0.1 mole of the dihalo- or the dihydroxy-terminated oligomer; also, about 0.120 moles of anhydrous sodium carbonate and about 0.010 moles of anhydrous potassium carbonate, as well as about 30 to 40 ml of xylene (the azeotroping agent) and about 80 to 100 gms of diphenyl sulfone (the dipolar aprotic solvent) are added into the flask. It should be noted that the amounts of solvents used will depend on the type and molecular weight of the oligomer. About 0.25 moles of the appropriate aminophenol (in the case when the dihalo oligomer is being used) or of the nitro-halobenzenoid compound (in the case when the dihydroxy-terminated oligomer is employed) are then charged. The equipment is evacuated and filled with nitrogen three times.

Heat is then applied to raise the temperature to 200° C. for one hour; the temperature is then raised to 250° C. where it is held for about 15 minutes, and then raised to the range of 280°–320° C. where it is held for 1 to 2 hours (generally about 0.5 hours at 280° C., 0.5 hours at 300° C. and one hour at 320° C.).

The cooled solid mass is ground to a fine granular material which is extracted with two 300 ml portions of boiling acetone, followed by two 500 ml portions of boiling water. The obtained end-capped oligomer is dried in vacuo till constant weight.

The prepared diamino poly(aryl ether ketones) are listed in Table I.

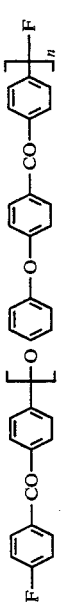

What is claimed is:

1. A process for the preparation of a diamino-terminated poly(aryl ether ketone) which consists of repeating units of one or more of the following formulae:

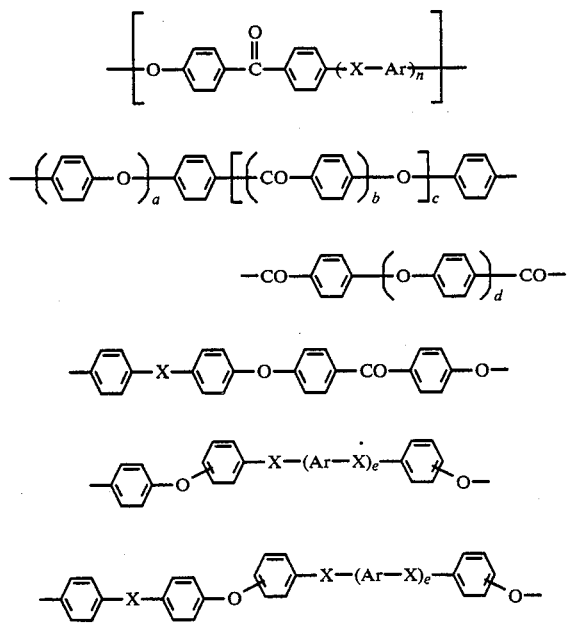

wherein Ar is independently a divalent aromatic radical selected from phenylene, biphenylene or naphthylene, X is independently O,

or a direct bond and n is an integer of from 0 to 3, b, c, d, and e are 0 to 1 and a is an integer of 1 to 4 which comprises reacting a corresponding dihalo-terminated oligomer with ammonia or a primary amine, in suspension or in solution at a temperature in a range from about 200° to about 350° C. in the presence of a catalyst which is a copper salt.

2. A process as defined in claim 1 wherein the primary amine is methylamine or phenylamine.

3. A process as defined in claim 1 wherein the catalyst is a cuprous salt in an amount in a range from about 0.01 to about 5 wt.% based on the dihalo-terminated oligomer.

4. A process as defined in claim 3 wherein the cuprous salt is cuprous chloride.

5. A process as defined in claim 3 which is carried out at a temperature in a range from about 250° to about 320° C.

6. A process as defined in claim 1 which is carried out in an aqueous suspension.

7. A process as defined in claim 1 which is carried out in a dipolar aprotic solvent.

8. A process as defined in claim 7 wherein the solvent is diphenyl sulfone.

9. A process as defined in claim 1 wherein at least 4 moles of ammonia are used per mole of the dihalo-terminated oligomer.

10. The process as defined in claim 1 wherein the ketimine groups formed during the reaction are post-hydrolyzed to the corresponding keto groups.

* * * * *

UNITED STATES PATENT AND TRADEMARK OFFICE
CERTIFICATE OF CORRECTION

PATENT NO. : 4,959,424
DATED : September 25, 1990
INVENTOR(S) : Markus Matzner and Donald M. Papuga It is certified that error appears in the above-identified patent and that said Letters Patent is hereby corrected as shown below:

| Col. | Line | |
|------|------|---|
| 2    | 8    | "touch" should read --tough--. |
| 4    | 18   | "and is" should read --and n is--. |
| 21   | 9    | "15.8 g" should read --15.86g--. |

Signed and Sealed this

Eighteenth Day of February, 1992

Attest:

HARRY F. MANBECK, JR.

*Attesting Officer*  *Commissioner of Patents and Trademarks*